United States Patent [19]
Harm et al.

[11] Patent Number: 4,734,198
[45] Date of Patent: Mar. 29, 1988

[54] DIALYSIS SOLUTION MIXING SYSTEM

[75] Inventors: William H. Harm, Columbia Heights; Larry E. Fuller, Minnetonka; Earnest R. Caine, Bloomington; Raymond F. Cracauer, Minneapolis; Louis C. Cosentino, Wayzata; F. Jesus Martinez, Plymouth, all of Minn.

[73] Assignee: Minntech Corporation, Minneapolis, Minn.

[21] Appl. No.: 577,387

[22] Filed: Feb. 6, 1984

[51] Int. Cl.⁴ .............................................. B01D 13/00
[52] U.S. Cl. .................................. 210/647; 210/96.2; 210/321.72
[58] Field of Search ................. 210/321.3, 96.2, 206, 210/282, 647; 366/159; 422/281, 283

[56] References Cited

U.S. PATENT DOCUMENTS

| | | | |
|---|---|---|---|
| 2,270,372 | 1/1942 | Hunter | 23/272 |
| 3,352,779 | 11/1967 | Austin et al. | 210/23 |
| 4,045,004 | 8/1977 | Berger | 366/159 |
| 4,116,834 | 9/1978 | King | 210/206 X |
| 4,265,760 | 5/1981 | Abel et al. | 210/282 |

FOREIGN PATENT DOCUMENTS 288421  5/1953  Switzerland .

Primary Examiner—Frank Spear
Attorney, Agent, or Firm—Vidas & Arrett

[57] ABSTRACT

A system and process for preparation of dialysis solution from dry chemicals and water on a large scale batch basis. The required amount of water is metered into a dialysis solution tank. Water from the tank is pumped into a spray head which is positioned above a shipping drum containing predetermined amounts of chemicals. Water rains down on the chemicals dissolving and/or entraining the same and the resulting slurry is returned to the dialysate tank as a slurry by means of a pickup wand and suction source. The liquid and chemicals in the dialysis solution tank are continually cycled until all the chemicals in the drum have been removed. Typically, an additional drum containing other kinds of chemicals is then added to the dialysis solution tank in the same manner. Circulation of the solution is continued within the tank until a fully uniform solution results. Dialysis solution in the tank is then filtered and checked for conductivity prior to its direct use in hemodialysis or dilution in a conventional proportioning system.

25 Claims, 5 Drawing Figures

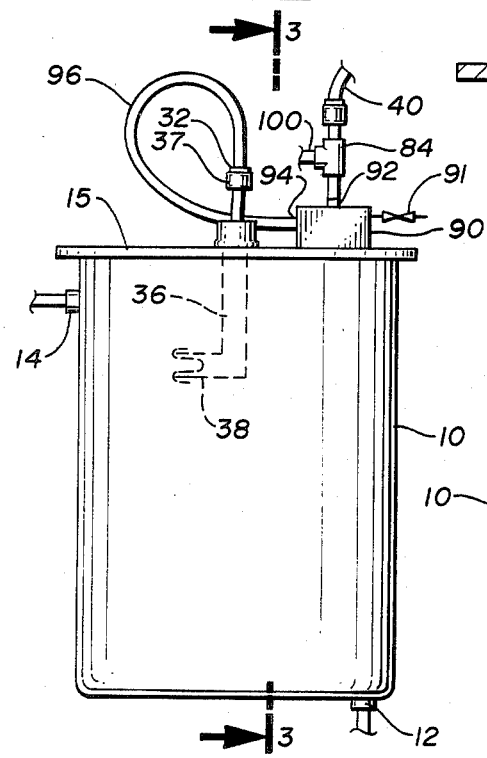
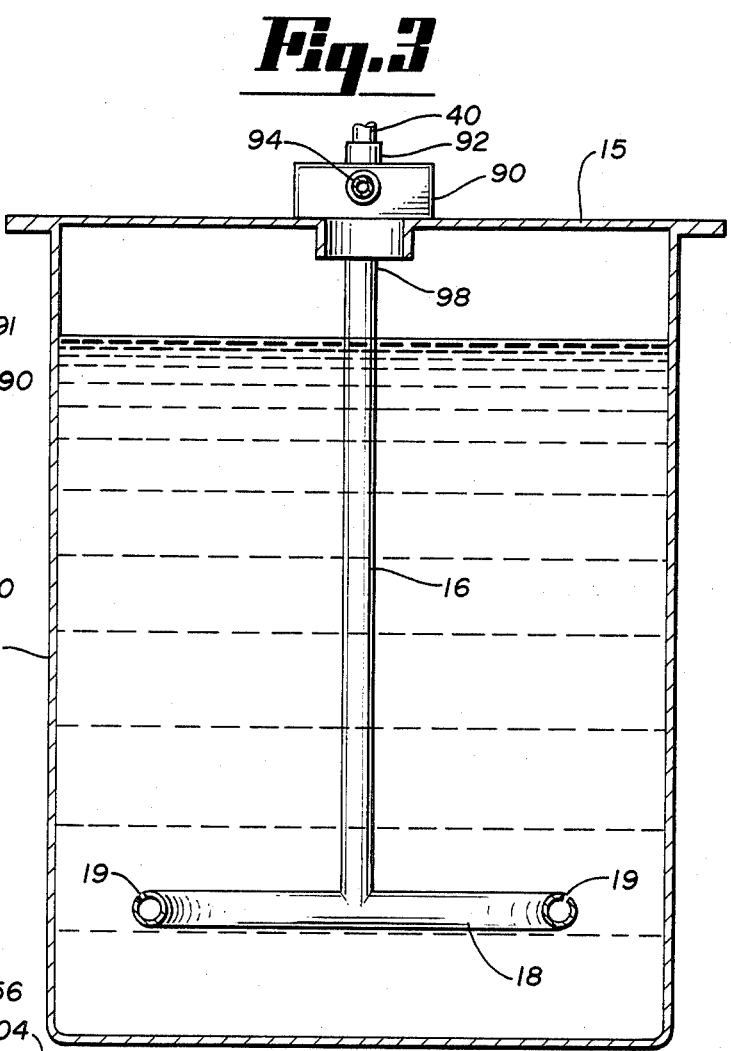
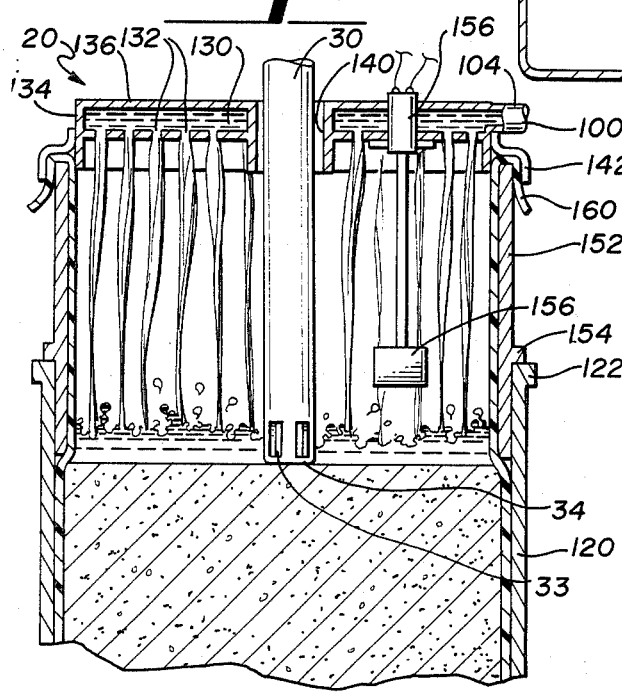
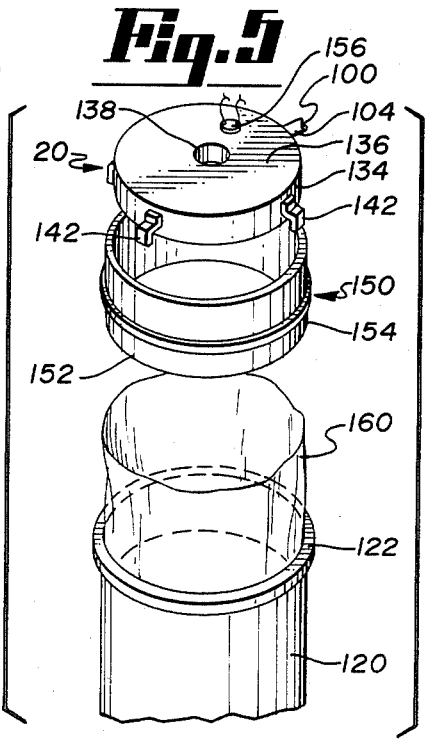

4,734,198

DIALYSIS SOLUTION MIXING SYSTEM

DESCRIPTION

1. FIELD OF THE INVENTION

This invention relates to an apparatus and the method of preparing and supplying hemodialysis solution from its bulk constituents of water and dry chemicals.

2. BACKGROUND OF THE INVENTION

Pre-mixed batches of dialysis solution supplied from an open tank by gravity head pressure to a number of artificial kidneys in large clinics have largely been replaced by systems designed to make up and supply dialysis solution only as needed by each individual artificial kidney. Dialysis concentrate and water are mixed in a venturi device in the direct supply line to a dialysis storage tank in U.S. Pat. No. 3,528,550. In U.S. Pat. Nos. 3,515,275 and 3,920,556 the use of positive displacement piston pumps in continuous dialysis solution supply systems for hemodialysis are disclosed.

Frequently, dialysis fluid for hemodialyzers is supplied by forming a mixture of a concentrated solution of dialysis chemicals from a reservoir with water in the ratio of approximately one part of concentrate to 34 parts water by volume. Proportioning devices must be capable of maintaining this concentration within prescribed limits for the duration of the hemodiaylsis treatment, which is on the order of 6 to 14 hours. Existing proportioning means utilized in dialysis solution delivery systems often utilize positive displacement mechanical devices, such as pistons or rotary pumps, in which separate pumps of different volumetric capacities are used to supply the concentrate and the water. These pumps are expensive, experience failures of moving seals, are mechanically complex and are subject to corrosion and salt deposit due in part to the highly concentrated solution.

It is often desirable to have large volumes of dialysis solution prepared for use by several patients. To prevent microbial contamination and caramelization of dextrose, the solution should not be stored for long periods of time.

Shipments of concentrated solutions of chemicals which are later diluted in proportioning systems are relatively expensive since a large volume of water must be shipped for each pound of dry chemical. Concentrated dialysis solutions may also experience undesirable precipitation of the chemicals. Thus, it is desirable for larger institutions to prepare their own dialysis solution from drums of dry chemicals using their own water supply.

BRIEF SUMMARY OF THE INVENTION

Accordingly to the present invention, there is provided a system and a method for preparing dialysis solution from water and shipping drums containing dry chemicals within a protective, water proof liner.

A dialysis solution tank is charged with a predetermined volume of water. Water within the tank is pumped into a spray head assembly which is placed atop an opened container of dry chemicals. In drums having a plastic bag liner, the plastic liner is lifted over an extender and forms a mixing space above the chemicals therewithin. The spray head assembly includes a spray plate containing numerous perforations through which water may pass. Water "rains" down into the drum on top of the chemicals causing the chemicals to dissolve and form a slurry.

A pickup wand is inserted through an opening in the spray head and spray plate and is used to suction the slurry of chemicals above the powdered chemicals out of the container and into the dialysis solution tank. The pickup wand preferably utilizes a jet pump employing the flow from a delivery pump to provide its suction. The slurry solution is delivered to the dialysis solution tank where it is mixed with the liquid within the tank. Continuous cycling back through the spray head continues until the shipping container is emptied.

The spray head is utilized until all of the chemicals within the shipping drum have been transported to the dialysis solution tank. Water flow into the drum is cut off and the drum is then emptied of all liquid. An additional drum containing chemicals such as calcium and magnesium chloride may then be emptied using the same process. After all the chemicals have been added, the pickup wand is disconnected. Its suction line is connected to a suction tube extending through an opening into the dialysis solution tank where its suction provides the motive force for filtration. Additional mixing within the dialysis solution tank is provided by air induced into the tank. Alternatively, a valve may be utilized to shift suction from the pickup wand to the tank suction tube. After thoroughly being mixed, the dialysis solution is pumped through a series of filters to be used directly or as concentrate in a proportioning mixing system. A series of pressure sensors, level sensors and valves are employed in the system which utilizes a master control to automate, to a major degree, the system.

The dialysis solution mixing system and process of the invention allows the preparation of large quantities of dialysis solution having a uniform chemical concentration. The batches may be made according to the weight of pre-packaged drums of chemicals which eliminate errors in measurement. The unique system of adding water to the chemicals insures that the dialysis solution within the dialysis solution tank will have a uniform concentration.

The system and process of the invention eliminates the requirement of receiving shipments of heavy containers of the concentrated dialysis solutions. Instead, drums of dry chemicals may be received at a fraction of the shipping weight of the prior systems. Expensive and possibly inaccurate proportioning systems which blend water with concentrate may be avoided by this invention. A batch may be simply and easily prepared shortly prior to its use with the assurance that its concentration will remain uniform. Alternatively, the system and process may prepare concentrated dialysis solution for use in existing proportioning systems. Controlled predilution, addition and mixing of the dry chemicals may be performed with less dedicated operator time.

BRIEF DESCRIPTION OF THE DRAWINGS

A detailed description of one preferred embodiment of my invention is hereafter described with specific reference being made to the drawings in which:

FIG. 2 is a side elevational view, partly in phantom, of the dialysis solution mixing system showing the suction connected to the dialysis solution tank;

FIG. 3 is a sectional view of the dialysis solution tank of FIG. 2 taken along lines 3—3 thereon;

FIG. 4 is a vertical sectional view of the spray head and chemical drum of FIG. 1; and FIG. 5 is an exploded perspective view of the spray head assembly of the invention.

DETAILED DESCRIPTION OF THE INVENTION

Figure 1:
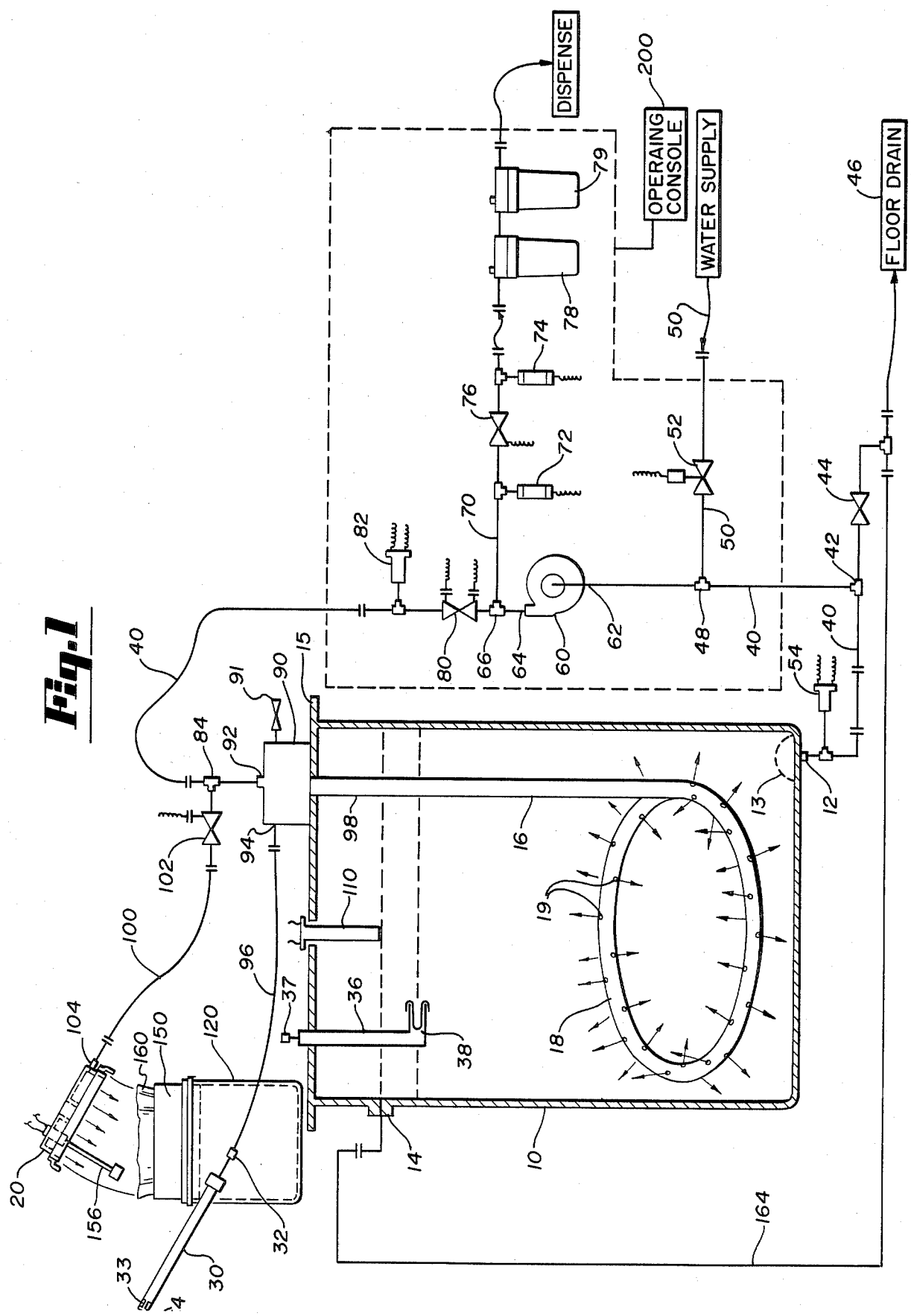
FIG. 1 is a schematic diagram of a dialysis solution mixing system according to the present invention.

The dialysis solution mixing system is illustrated in FIGS. 1 and 2. Generally, the system consists of a dialysis solution tank 10, a spray head assembly 20, and a pickup wand 30. Fluid connecting means join the three.

The dialysis solution tank 10 may be a generally cylindrically shaped tank. The tank volume is dependent only on the user's desires. A tank volume may be selected which allows the use of the contents of a standard shipping drum of dialysis chemicals which avoids weighing out a quantity of chemicals.

The tank includes a drain 12 that allows the tank to completely empty. An overflow drain 14 is also preferably provided high on the tank walls and is connected by overflow line 164 to drain 46. The tank drain 12 is connected to dialysis tank delivery line generally indicated as 40 which includes a tee 42 and a drainage valve 44 that leads to floor drain 46. Tank drain 12 preferably includes a removable drain screen 13 which prevents large particles from entering line 40. Delivery line 40 branches at tee 48 to a water supply line 50 which includes water supply valve 52.

A level sensor 54 is provided in delivery line 40 beneath tank drain 12. The level sensor 54 may be of the ultrasonic type such as the air and foam detector described in U.S. Pat. No. 4,068,521 to Cosentino et al.

The delivery line 40 branches at tee 48 and leads to a pump 60 having an inlet port 62 and discharge port 64. Pump 60 may be a rotary displacement pump or and pump capable of handling dialysis solution.

The delivery line 40 proceeds from pump 60 to tee 66 where it splits and joins dialysis fluid delivery line 70. The dialysis fluid delivery line 70 includes a low pressure sensor 72, high pressure sensor 74, valve 76 and delivery line filters 78 and 79. The dialysis delivery line delivers prepared dialysis solution for direct patient use or as concentrate to be diluted in conventional proportioning systems, shown schematically as the dispensing box in FIG. 1. Conductivity of the solution and other parameters of the dialysis solution are desirably checked at this point before utilizing the dialysis solution for treatment.

The delivery line 40 includes a delivery line valve 80 and a level sensor 82, which may be of the same type as level sensor 54, as shown in FIG. 1. Delivery line 40 branches at tee 84 where one leg proceeds to the pressure inlet port 92 of a jet pump 90 and the other leg of the tee is connected to the spray head line 100.

The spray head line 100 includes a valve 102 and enters the spray head assembly 20 through inlet 104. The spray head assembly will be described below.

The suction port 94 of the jet pump 90 is connected to a flexible conduit 96 which in turn is connected to a hollow pickup wand 30 by means of a disconnect coupling 32. The wand is formed of a rigid, hollow suction tube and is preferably manually held and operated. Any suction wand that can pick up a mixture of chemicals and water may be utilized and may include wands that "walk" within a container so as to accelerate the chemical pick-up process. Preferably, a solid plug 34 extends below the openings 33 of wand 30 such that the plug functions to prevent plugging of the wand. The function of the wand will be described more fully below.

A second fixed suction pipe 36 penetrates tank top 15. Suction pipe 36 includes a coupling 37 which may be connected to conduit 96. Suction pipe 36 may include an open mesh sock 38 at its lower end and serves to break up foam and to entrap foreign matter entering the pipe.

The discharge port 98 of the pump 90 is connected to supply pipe 16 which enters tank 10 and descends to a toroidal hollow ring 18 which is situated above the tank 10 bottom. The toroid includes a plurality of perforations 19 throughout its surface which serve to provide a mixing action when fluid passes from the toroid into the tank. Alternatively or additionally, the mixing action within tank 10 may be supplied by mechanical stirring devices.

The addition of air into the solution entering tank 10 through line 16 increases the mixing action within tank 10. Air is ordinarily picked up through suction wand during its operation. Pump 90 may be constructed with a second suction inlet controlled by a manual air bleeder valve 91. Air bleeder valve 91 may be adjusted to introduce air into line 16. Alternatively, the air bleeder may be a simple, preset orifice.

In operation, tank 10 is charged with deionized, ANSI standard hemodialysis quality water by opening valve 52. Water fills the tank to a predetermined level which may be indicated by an electrical level sensor 82 whose signal causes the solenoid on valve 52 to shut off the water flow. Level sensor 82 may also protect pump 60 from running dry by preventing pump 60 from running unless fluid is indicated above pump 60 at level sensor 82. Preferably, the tank is pre-filled with less than the required volume of water.

After all the chemicals have been added and mixed, the remaining water is then added and mixed in a manner not unlike using a volumetric flask. If the final tank volume is 55 gallons the pre-fill level may desirably be set at 40 gallons.

An operator then positions the spray head assembly 20 over the rim 122 of an opened chemical container 120. The chemicals which are most often used in hemodialysis are sodium chloride, sodium bicarbonate or sodium acetate, dextrose, calcium chloride, potassium chloride and magnesium chloride. Calcium and magnesium chloride are normally added later from a second drum to avoid precipitation of the calcium.

Spray head assembly 20 as best shown in FIGS. 4 and 5, includes a spray plate 130 which is perforated with many holes 132 through which water may pass. Preferably, spray plate 130 is formed from polypropylene or similar corrosion-resistant material. The outer periphery of the spray plate 130 is attached in fluid tight communication to an outer shell 134 which circles the plate. The upper edge of outer shell 134 is preferably attached to an upper header 136 which substantially covers the spray plate 130. Spray head assembly 20 defines a chamber in which water is introduced. The chamber prevents fluid from splashing outside of the spray head.

Both the spray plate 130 and upper header 136 include a perforation 138 in the center through which the wand 30 may extend. A core shell 140 joins the periphery of the wand perforation 138 in the spray plate 130 and the upper header 136 together. The core shell 140 provides support to the spray head assembly and defines the space through which fluid entering inlet 104 passes.

Preferably, the spray head assembly is fabricated from polypropylene or similar corrosion resistant material and the individual parts are welded together.

The spray head assembly 20 may rest directly on a container rim 122 through the use of angular support legs 142 which are attached to outer shell 134. More preferably, the spray head assembly 20 with legs 142 is positioned on top of a drum height extender 150. The container height extender 150 consists of extender walls 152 and a container rim positioning stop 154 which rests upon the drum rim 122. A protective liner 160 within the drum may simply be lifted up and over the extender 150 so as to effectively provide a higher, water-proof drum. The empty space is used to form a splash shield and to increase the speed at impact of water onto the chemicals within the drum below the spray head. Of course, drums that are not fully filled would have sufficient space above the chemicals without the addition of the extender.

Delivery line valve 80 and spray head valve 102 are opened and pump 60 is turned on. Water enters the spray head assembly 20 from dialysis solution tank 10 and "rains" down on the dry chemicals within container 120 through spray plate 130. A float 156 having a sealed reed switch is also carried by the spray head assembly and prevents water within container 120 from overflowing by providing a signal which causes valve 102 to close or stops pump 60.

An operator positions wand 30 through the wand perforation 138 in the spray head assembly. The solid plug 34 rests directly on the dry salt and tends to act to prevent the suction of dry chemicals through the wand which might otherwise lead to plugging of the wand and hose. The slurried chemicals immediately above the dry chemicals in the drum are picked up by the wand through openings 33. The wand tends to dig into the chemicals within the drum forming a depression and tends to support itself. Chemicals which are dissolved in suspended form within the drum are picked up by the wand 30 and carried into tank 10 where they become fully dissolved. The efficiency of the system is enhanced if the spray directly impacts on the chemicals within the drum. Valve 102 may be manually adjusted to decrease the flow of water through the spray head onto the chemicals to prevent the accumulation of an excessive liquid layer in the drum.

Ordinarily, the suction provided by wand 30 removes water within the drum at a rate which is faster than water enters the drum through perforations 132. Wand 30 picks up both air and a chemical slurry which are then delivered into tank 10.

The air and slurry of chemicals are carried into tank 10 through toroid 18 and perforations 19. The toroid and its perforations increase the mixing action within the tank. The amount of air entering tank 10 may be adjusted through the use of air bleeder valve 91 or by adjusting the flow to the spray head.

The process continues, with solution from tank 10 continuously replacing the solution and chemicals removed from container 120 by the wand 30. Eventually, all the chemicals are removed from within container 120. At this time, valve 102 is closed and wand 30 empties container 120. The next container of chemicals may then be solubilized and emptied as described above.

Ideally, the tank is designed such that its volume is set for the standard size and weight drums of chemicals used. Thus, for example, a 200-pound drum of chemicals could be used in its entirety without the need to weigh a set amount of chemicals into another container. The second container would preferably contain chemicals having properties which dictate their later addition to avoid precipitation.

Pickup wand 30 is disconnected from flexible conduit 96. Flexible conduit 96 is then connected to coupling 37 of suction pipe 36. The fluid within tank 10 is pulled through suction pipe 36 and cycled back through the mixing toroid 18. The normal foam which tends to build up in the tank during mixing is broken up when it passes through open mesh sock strainer 38.

Tank 10 is then filled to its final volume with additional water. The tank is filled until it reaches level sensor 110 whose signal causes valve 52 to close. The dialysis solution within the tank is then mixed.

After thoroughly mixing, the dialysis solution leaves tank 10 through delivery line 40 and is filtered prior to use. The conductivity of the dialysis solution is then checked with a meter such as the RS-2100A dialysis solution meter from Renal Systems, Inc. of Minneapolis, Minn. Preferably, a coarse ten micron filter 78 is employed immediately before a fine, one micron filter 79 to remove any large contaminants. A high pressure sensor 74 is used to monitor the condition of filters 78 and 79. If the filters become clogged, the pressure rises and sensor 78 sends a signal to a controller 200 which may indicate the condition and/or shut the system down for filter replacement.

A low pressure sensor 72 is preferably provided provide an indication of suction conditions and the operation of pump 60. An operator may be alerted of insufficient pressure by a signal from low pressure sensor 72. The pump may then be shut off manually or automatically to prevent damage from its running without solution.

The dialysis solution mixing system and process may be operated manually or more preferably, automated with the use of known controllers. For example, a controller 200 may receive condition signals from level and pressure sensors which in turn causes valves and pumps to be automatically controlled.

A suitable controller 200 may include a power switch, a circulation switch which causes the dialysis solution to cycle and mix prior to or during delivery and a dispensing switch. The dispensing switch may include an indicator light which indicates that tank 10 is empty when level sensor 54 senses air instead of fluid.

Operator mixing controls may include an on/off switch which initially fills tank 10 to the height indicated by level sensor 82 and then activates pump 60 and opens valve 80 and 102 when a second switch is depressed. Indicator lights may identify the stage of the process and automatic timers may control the mixing time.

A variety of system alarms may be included to indicate that the tank is full as sensed by level sensor 110, a restriction in the wand, high filter pressure as indicated by pressure sensor 74, low pump pressure as indicated by pressure sensor 72 and the like.

Generally, all valves may be solenoid controlled, normally closed valves which open when energized from the controller. At start-up, an empty tank signal from level sensor 54 may be used to cause water supply valve 52 to open. The same valve may be closed only when the solenoid is de-energized upon a signal that the tank is full of water from level sensor 82 for initial fill and 110 for final fill. Also, manual overrides may be included as desired.

All of the controls which automate the system may be readily added and custom tailored by those skilled in the art. The controllers per se do not form a part of this invention.

In considering this invention, it should be remembered that the present disclosure is illustrative only and the scope of the invention should be determined by the appended claims.

What is claimed is:

1. A blending system for preparation of dialysis solution from water and dry chemicals comprising:
   (a) a dialysis solution tank;
   (b) diluent means for supplying water into said tank;
   (c) slurry means for conveying liquid from said tank to a source of dry chemicals, said slurry means including a chamber defining means for directing water onto said chemicals within said source container;
   (d) said chamber defining means being constructed and arranged such that water is forced through a plurality of perforations in a plate forming the bottom of said chamber defining means so as to form a slurry of chemicals therebelow;
   (e) suction means for conveying said slurry from said source to said dialysis solution tank including a hollow tubular pickup tube and a suction source;
   (f) dialysis solution tank mixing means for mixing said chemicals within said tank; and
   (g) delivery means for delivering mixed dialysis solution from said tank to a dispensing station.

2. The blending system of claim 1 wherein said mixing means includes a hollow toroidal ring within said tank and having a plurality of perforations, said toroidal ring being connected in fluid relation to the output from said suction means such that a slurry of water and chemicals enters said toroidal ring and passes through said perforations into said tank.

3. The blending system of claim 2 wherein said chamber defining means includes a chamber having a lower lip constructed and arranged such that said chamber is positionable above the upper rim of said chemical source container.

4. The blending system of claim 2 wherein said mixing means includes air bleed means being constructed and arranged for controllably introducing air into said toroidal ring so as to increase the agitation and mixing within said ring and tank.

5. The blending system of claim 2 wherein said suction means hollow tubular pickup tube includes a tip projecting beyond the open suction end of said tube such that said tip rests directly on the surface of said dry chemicals thereby functioning as a vacuum breaker if no slurry is present above the dry chemicals.

6. A blending system for preparation of hemodialysis solution from a diluent of water and from dry chemicals comprising:
   (a) a dialysis solution tank;
   (b) diluent means for supplying water into said tank;
   (c) level sensing means within said tank for determining when said tank is charged with diluent and for controlling the flow of diluent into said tank;
   (d) delivery means for conveying liquid within said tank to a source of a predetermined quantity of dry chemicals having the amount of chemicals required to make up the hemodialysis solution;
   (e) said delivery means including solubilizing means to direct said diluent onto said dry chemicals so as to form a slurry of chemicals and diluent;
   (f) level sensing means for controlling the introduction of diluent into said source of dry chemicals;
   (g) pickup wand means for conveying said slurry and diluent from said chemical source to said dialysis solution tank;
   (h) dialysis solution tank mixing means for receiving and mixing said chemicals within said tank from said pickup wand means; and
   (i) dialysis solution delivery means for delivering mixed dialysis solution from said dialysis solution tank for dialysis including filters, pressure sensors, monitors for determining the concentration of said dialysis solution and valves controlled by outputs of said sensors and monitors.

7. A system for preparing dialysis solution from diluent water and dry chemicals comprising:
   (a) a dialysis solution tank;
   (b) diluent means for supplying water into said tank;
   (c) a source of dry chemicals;
   (d) delivery means for conveying diluent within said tank to said source of chemicals; said delivery means including a spray head means for directing a spray of diluent into said source of dry chemicals so as to cause the chemicals to dissolve and form a slurry;
   (e) pickup wand means for conveying said slurry within said chemical source to said dialysis solution tank;
   (f) dialysis solution tank mixing means for receiving said slurry from said pickup wand means and for mixing same within said tank; and
   (g) dialysis solution delivery means for delivering mixed dialysis solution from said dialysis solution tank for use in dialysis.

8. A system for preparation of hemodialysis solution from water and chemicals comprising:
   (a) a dialysis solution tank including a water inlet and drain outlet;
   (b) diluent means for supplying water into said tank through said water inlet;
   (c) delivery means for conveying water within said tank through said drain outlet and into a container of dialysis solution chemicals so as to solubilize and entrain said chemicals in a slurry;
   (d) wand means for conveying said slurry within said container into said dialysis solution tank;
   (e) dialysis solution tank mixing means for mixing said slurried chemicals within said dialysis solution tank; and
   (f) dialysis solution delivery means for delivering mixed dialysis solution from said dialysis solution tank for use in dialysis.

9. The system of claim 8 wherein said diluent means includes valve means for controlling fluid flow to said tank, said valve means being connected to a control means which opens and closes said valve means in response to a signal from a level sensor means within said tank.

10. The system of claim 8 wherein said delivery means includes valve means for controlling fluid flow from said tank, said valve means being connected to a control means which controls said valve means in response to a signal from a level sensor means associated with said drain outlet.

11. The system of claim 8 wherein said delivery means includes a spray head means for directing a spray of water into said container of dialysis solution chemicals so as to cause the chemicals to dissolve and become suspended in said water.

12. The system of claim 11 wherein said spray head means includes a spray head comprising a spray plate constructed and arranged to be positionable above an open salt container and having a plurality of perforations therethrough, such that water may pass in a relatively uniform, rain-like spray over the upper surface of chemicals within said container.

13. The system of claim 12 wherein said spray head further includes an opening through said spray plate through which said wand means may extend therethrough into said container, said opening being defined by an upstanding raised lip such that water passes through said perforations but not through said opening.

14. The system of claim 12 wherein said spray head includes a level sensor which extends below said spray plate into the container, said level sensor being constructed and arranged for sending a signal to a control means which controls the delivery of water into said container by controlling said delivery means.

15. The system of claim 14 wherein said spray head means includes an extension means for positioning said spray plate above the container and being constructed and arranged such that water passing through said spray plate perforations is directed within said container.

16. The system of claim 14 wherein said spray head means includes a container height extender, said extender being constructed and arranged with vertically extending walls that are supported by the top rim of said container such that the effective height of the container above the chemicals therewithin is increased, said height extender further being constructed and arranged such that a water proof liner within said chemical container may be pulled up and over said extender such that a waterproof barrier is formed above the level of the chemicals therewithin.

17. The system of claim 15 wherein said spray head means includes a cover means for excluding dust and containing splashed water and said cover means being constructed and arranged with a perforation through which said wand may pass therethrough.

18. A method for preparing hemodialysis solution from a diluent of water and from dry chemicals comprising:
(a) metering diluent into a dialysis solution tank;
(b) conveying said diluent from said tank onto a source of a predetermined quantity of dry chemicals having the amount of chemicals required to make up the hemodialysis solution;
(c) conveying the solubilized and dispersed chemicals from said source to said dialysis solution tank;
(d) mixing said diluent and chemicals within said dialysis solution tank;
(e) continuing said conveying of diluent which now contains chemicals from said tank to said chemical source and said slurried chemicals to said dialysis solution tank until all of said chemicals have been conveyed to said tank; and
(f) mixing said chemicals within said tank until a uniform concentration is obtained therewithin.

19. A method for preparing hemodialysis solution from a diluent of water and from dry chemicals comprising:
(a) filling a dialysis solution tank with a predetermined amount of water;
(b) conveying said water from said tank into a predetermined quantity of dry chemicals within a container on top of said chemicals;
(c) conveying the solutilized and dispersed chemicals within said container to said dialysis solution tank continuously during the conveyance of water and water containing chemicals to said container;
(d) discontinuing said conveyance of water and water containing chemicals to said container when all the chemicals within said container has been removed; and
(e) mixing said chemicals within said dialysate tank until a uniform chemical concentration is achieved.

20. The process of claim 19 wherein said water from said dialysis solution tank is sprayed downwardly onto chemicals within said container from above.

21. The process of claim 19 wherein solubilized chemicals and chemicals in a slurry with water are conveyed from said container to said dialysis solution tank by suction through a pickup wand.

22. The process of claim 19 wherein said solubilized chemicals within said dialysis solution tank are mixed by forcing said chemicals entering the tank through a toroid containing a plurality of perforations located adjacent the tank floor.

23. The process of claim 22 wherein air is introduced into the chemicals entering said tank and toroid so as to increase the mixing action within the tank.

24. The process of claim 19 wherein water is conveyed from said tank into the space above said container created by extending a plastic liner within said container over an extender that increases the effective height of said container.

25. The process of claim 19 wherein said chemicals are first conveyed into said dialysis solution tank from said container and a second container of chemicals comprising calcium salts is then conveyed into said tank.

* * * * *

UNITED STATES PATENT AND TRADEMARK OFFICE
CERTIFICATE OF CORRECTION

PATENT NO. : 4,734,198

DATED : March 29, 1988

INVENTOR(S) : WM. HARM, LARRY E. FULLER, ET AL

It is certified that error appears in the above-identified patent and that said Letters Patent is hereby corrected as shown below:

Col. 3, line 67, delete "chem1-" and insert - "chemi-"

Col. 5, line 23, delete "contairer" and insert - container-

Signed and Sealed this

Twenty-third Day of August, 1988

Attest:

DONALD J. QUIGG

Attesting Officer     Commissioner of Patents and Trademarks